United States Patent [19]

Yanagi et al.

[11] Patent Number: 5,530,135
[45] Date of Patent: Jun. 25, 1996

[54] PROCESS FOR THE PRODUCTION OF 1-SUBSTITUTED-5(4H)-TETRAZOLINONES

[75] Inventors: Akihiko Yanagi, Tochigi; Yukiyoshi Watanabe, Saitama; Shin-ichi Narabu, Ibaraki, all of Japan

[73] Assignee: Nihon Bayer Agrochem K.K., Tokyo, Japan

[21] Appl. No.: 283,103

[22] Filed: Jul. 29, 1994

[30] Foreign Application Priority Data

Aug. 5, 1993 [JP] Japan .................................. 5-212153
May 23, 1994 [JP] Japan .................................. 6-130873

[51] Int. Cl.$^6$ .................................................. C07D 257/04
[52] U.S. Cl. .................................................. 548/251
[58] Field of Search .................................................. 548/25

[56] References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,913,724 | 4/1990 | Poss | 71/92 |
| 5,138,068 | 8/1992 | Ehrenfreund et al. | 548/251 |

OTHER PUBLICATIONS

J. Org. Chem, vol. 45, pp. 5130–5136, 1980, Tsuge, et al. "Reactions of Trimethylsiyl Azide with Heterocumulenes".
J. Am. Chem., vol. 81, pp. 3076–3079, 1959, Howitz, et al. "The synthesis of 1–Substituted 5 (4H) Tetrazolines".

*Primary Examiner*—David B. Springer
*Attorney, Agent, or Firm*—Sprung Horn Kramer & Woods

[57] ABSTRACT

1-Substituted-5(4H)-tetrazolinones of the formula (I)

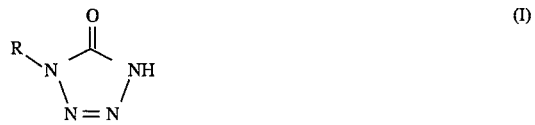

wherein R is alkyl, haloalkyl, cycloalkyl, phenyl, substituted phenyl or aralkyl, are obtained in very good yields by reacting, in a polar solvent, an isocyanate of the formula R-NCO (II) with sodium azide ($NaN_3$) in a molar ratio of 1:1 and in the presence of aluminum chloride ($AlCl_3$), followed by the addition of water and a mineral acid in excess.

4 Claims, No Drawings

PROCESS FOR THE PRODUCTION OF 1-SUBSTITUTED-5(4H)-TETRAZOLINONES

The present invention relates to a process for the production of 1-substituted-5(4H)-tetrazolinones.

Tetrazolinone derivatives can be employed as industrially useful active substances such as medicines, agricultural chemicals, etc., for example, as disclosed in Japanese Patent Application Publication No. Hei-2-24272, for example. For production 1-substituted-5-(4H)-tetrazolinones, starting materials for the above-mentioned tetrazolinone derivatives, J. Am. Chem. Soc., vol. 81, p.p. 3076–3079 (1959) discloses a process wherein an isocyanate selected from a number of isocyanate derivatives is reacted with sodium axide in tetrahydrofuran and in the presence of aluminum chloride.

However, that process has such disadvantages that, to obtain a good yield, use must be made of as much as three equivalents of sodium axide per equivalent of isocyanate as well as of tetrahydrofuran as the solvent. That is a very expensive compound, so it is not attractive in view of industrial and economical considerations to employ that process.

Further, a process is disclosed in J. Org. Chem. vol. 45, p.p. 5130–5136 (1980), wherein an isocyanate selected from a number of isocyanate derivatives is reacted with trimethylsilyl azide but this process has also been found to be inappropriate industrially because trimethylsilyl azide is an expensive material and about two equivalents must be used per equivalent of isocyanate to obtain a satisfactory yield, further requiring such severe reaction condition as refluxing under heating in the absence of solvent.

To solve these problems, there has now been found a process for the production of 1-substituted-5(4H)-tetrazolinones of the general formula (I)

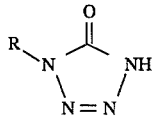
(I)

wherein
R is alkyl, haloalkyl, cycloalkyl, phenyl, or substituted phenyl or aralkyl,
wherein comprises reacting, in a polar solvent, an isocyanate of the general formula (II)

RNCO  (II)

with sodium azide in approximately equimolar ratio and in the presence of aluminum chloride, followed by addition of water and a mineral acid in excess.

According to this process where use is made, as a polar solvent, of N,N-dimethyl formamide, for example, it has been unpredictably found that the desired 1-substituted-5(4H)-tetrazolinones are obtained in good yield and, as a result, this process is suitable for use on industrial scale.

Advantageously R is $C_{1-6}$ alkyl, $C_{1-4}$ alkyl substituted by halogen, such as fluorine, chlorine or bromine, $C_{3-8}$ cycloalkyl, benzyl, phenethyl, phenyl, or phenyl substituted by $C_{1-4}$ alkyl, halogen, nitro, cyano, $C_{1-4}$ alkoxy, $C_{1-4}$ alkoxycarbonyl, $C_{1-4}$ alkylthio, phenoxy, $C_{1-4}$ haloalkoxy or $C_{1-4}$ haloalkylthio.

When, for example, 2-chlorophenyl isocyanate and sodium azide, are employed as starting materials, the reaction is illustrated by the following equation:

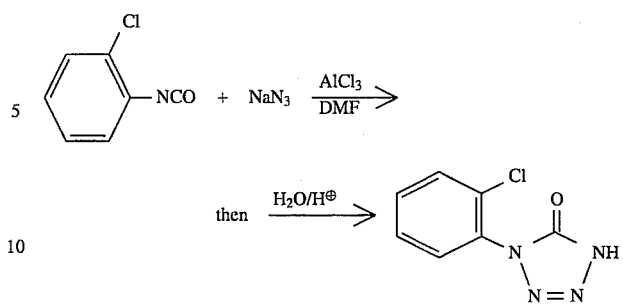

Representative isocyanates (II) include: ethylisocyanate, n-propylisocyanate, t-butylisocyanate, 2-chloroethylisocyanate, 3-chloropropylisocyanate, cyclopentylisocyanate, cyclohexylisocyanate, benzylisocyanate, phenylisocyanate, 2-chlorophenylisocyanate, 2-chloro-6-methylphenylisocyanate, 2-trifluoromethylphenylisocyanate, o-tolylisocyanate, 2-nitrophenylisocyanate, 2-cyanophenylisocyanate, 2-methoxyphenylisocyanate, 2-trifluoromethoxyphenylisocyanate, 2-trifluoromethylthiophenylisocyanate, 2-bromophenylisocyanate, 2-methylthiophenylisocyanate, 2-ethylphenylisocyanate, 2-isopropylphenylisocyanate, 2,6-dimethylphenylisocyanate, 2-ethyl-6-methylphenylisocyanate, 2-fluorophenylisocyanate, 2,6-diethylphenylisocyanate, 2,6-dichlorophenylisocyanate, 2,4-dichlorophenylisocyanate, 2,5-dichlorophenylisocyanate, 2,4,6-trichlorophenylisocyanate, 2,4,6-trimethylphenylisocyanate, 4-bromo-2,6-dimethylphenylisocyanate, 2-phenoxyphenylisocyanate, phenethylisocyanate, 3-chloro-4-trifluoromethylphenylisocyanate, 2-chloro-4-trifluoromethylphenylisocyanate, etc.

Representative polar solvents include N,N-dimethyl formamide, N,N-dimethyl acetamide, N-methylpyrrolidone and 1,3-dimethylimidazolinone, etc., preferably N,N-dimethyl formamide.

In carrying out the process with N,N-dimethyl formamide as polar solvent, for example, one mol of an isocyanate of the general formula (II) is reacted with 0.8 to 1.3 mols, preferably 1 mol, of sodium azide and 0.005 to 1.5 mols of aluminum chloride, preferably catalytic amount of 0.01 to 1.0 mol at a reaction temperature from about 0° C. to about 200° C., preferably from about 25° C. to about 150° C., and normal pressure for about 2 to 24 hours, preferably about 3 to about 10 hours.

The process according to the present invention is illustrated in the following non-limiting examples.

EXAMPLES

Synthesis Example 1

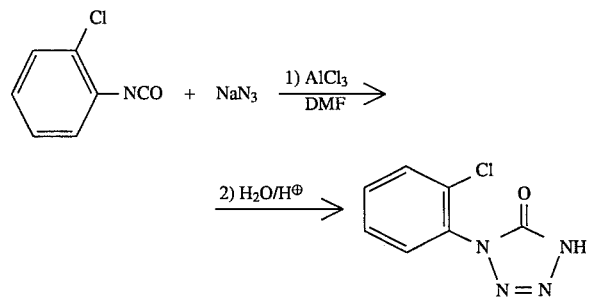

Anhydrous aluminum chloride (1.5 g) was added to N,N-dimethylformamide (20 ml) under ice cooling and the resulting mixture was stirred for fifteen minutes. To the mixture was added sodium azide (0.65 g), followed by a 15 minute-stirring, addition of 2-chlorophenylisocyanate (1.53 g) and heating at 70° to 75° C. for three hours, in that order. After cooling, the reaction mixture was added with stirring to a mixture of sodium nitrite (1 g), water (200 ml) and ice (100 g) and the resulting mixture was acidified was 10% hydrochloric acid (until a potassium iodide starch paper became discolored), followed by extraction with ethyl acetate. The thus obtained ethyl acetate layer was washed with water, dried over sodium sulfate and evaporated under reduced pressure. The resulting residue was purified by flash column chromatography (eluent: hexane:ethyl acetate = 2:1) to obtain the desired 1-(2-chlorophenyl)-5(4H)-tetrazolinone (1.8 g) having a m.p. in the range of from 124.5° C. to 125.5° C. in a yield of 92% of theory.

Synthesis Example 2

Synthesis of 1-(2-chlorophenyl)-5(4H)-tetrazolinone by decreasing the amount of $A\lambda C\lambda_3$ To a mixture composed of $NaN_3$ (1.95 g) and DMF (9 m$\lambda$), anhydrous aluminum chloride (0.2 g) was added portionwise at ice bath temperature and under argon stream, and the resultant mixture was stirred at 70°~75° C. for 15 minutes. To the mixture was added 2-chlorophenylisocyanate (4.71 g), and the whole was stirred at 70°~75° C. for 4 hrs.

The cooled reaction mixture was pursed onto a mixture composed of sodium nitrite (1 g), water (200 m$\lambda$) and ice (50 g), and the whole was made acidic by addition of concentrated hydrochloric acid until a potassium iodide-starch reaction became positive. The resultant mixture was extracted with ethyl acetate (100 m$\lambda$× 3). The combined ethyl acetate extract was washed with water, dried over anhydrous sodium sulfate and evaporated.

The residue was subjected to silica gel flash column chromatography (n-hexane:AcOEt = 2:1) to give the desired 1-(2-chlorophenyl)-5(4H)-tetrazolinone (5.8 g).

Yield: 98% mp: 124.5°~125.5° C.

In analogous manner, there were obtained the following compounds shown in Table 1 in a yield of at least 90% of theory.

TABLE 1

(I)

| Example No. | R | Physical properties m.p./$n_D^{20}$ (°C.) |
|---|---|---|
| 2 | n-$C_3H_7$— | 45–47.5° C. |
| 3 | $ClCH_2CH_2$— | 79.5–81.5° C. |
| 4 | iso-$C_3H_7$— | 105–107° C. |
| 5 | t-$C_4H_9$— | 105–106.5° C. |
| 6 | $ClCH_2$— | 1.5091 |
| 7 | $ClCH_2CH_2CH_2$— | 49.5–53° C. |
| 8 | cyclohexyl-H | 118.5–120° C. |

TABLE 1-continued (I)

| Example No. | R | Physical properties m.p./$n_D^{20}$ (°C.) |
|---|---|---|
| 9 | benzyl (Ph-$CH_2$—) | 141–143.5° C. |
| 10 | phenyl | 180–183.5° C. |
| 11 | 2-F-phenyl | 1.5153 |
| 12 | 2-Br-phenyl | 142.5–146° C. |
| 13 | 2-$CH_3$-phenyl | 142.5–144.5° C. |
| 14 | 2-$C_2H_5$-phenyl | 114.5–117° C. |
| 15 | 2-$C_3H_7$-iso-phenyl | 1.5249 |
| 16 | 2-$OCH_3$-phenyl | 157.5–159.5° C. |
| 17 | 2-$SCH_3$-phenyl | 132–133.5° C. |
| 18 | 2-$NO_2$-phenyl | 123.5–125° C. |

TABLE 1-continued $$\begin{array}{c} O \\ \| \\ R-N-C \\ | \quad \quad \backslash NH \\ N=N \end{array}$$ (I)

| Example No. | R | Physical properties m.p./$n_D^{20}$ (°C.) |
|---|---|---|
| 19 | 2,6-dimethylphenyl | 143.5–147.5° C. |
| 20 | 2,6-diethylphenyl (2-C$_2$H$_5$, 6-CH$_3$)... 2-ethyl-6-methylphenyl | 107–111° C. |
| 21 | 2,6-diethylphenyl | 93.5–96° C. |
| 22 | 2-methyl-6-chlorophenyl | 121–124° C. |
| 23 | 2,6-dichlorophenyl | 148.5–152° C. |
| 24 | 2,3-dichlorophenyl | 176–180° C. |
| 25 | 2-chloro-4-trifluoromethylphenyl | 166–168° C. |
| 26 | 2,4-dichlorophenyl | 141.5–145° C. |
| 27 | 2,5-dichlorophenyl | 164.5–166° C. |
| 28 | 2,4,5-trichlorophenyl | 156–158.5° C. |
| 29 | 2,4,6-trimethylphenyl | 153–156° C. |
| 30 | 4-bromo-2,6-dimethylphenyl | 189–192.5° C. |
| 31 | 2-chloro-4-nitrophenyl (approx.) | 171–173° C. |

Experiments were conducted in the same Syntheses Example 2, provided that an amount of anhydrous aluminum chloride was varied.

The yield of the desired 1-(2-chlorophenyl)-5(4H)-tetrazolinone was kept at the practically acceptable high level, shown in Table 2

TABLE 2

| AlCl$_3$ (g) | ratio | Reaction time (hr) | Yield (%) |
|---|---|---|---|
| 1.49 | (0.37) | 3 | 98 |
| 0.4 | (0.1) | 4 | 99 |
| 0.2 | (0.05) | 4 | 98 |
| 0.04 | (0.01) | 5 | 94 |

Note: The number of "ratio" means a molar quantity of AlCl$_3$ per a mol of an isocyanate of the general formula (II).

Comparative Synthesis Example 1 (by the process disclosed in J. Am. Chem. Soc., vol. 81, p. 3076, 1959)

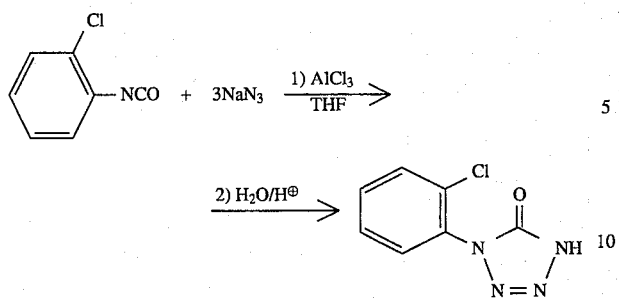

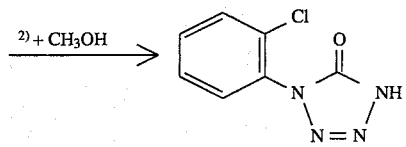

Anhydrous aluminum chloride (1.5 g) was added to tetrahydrofuran (30 ml) with ice bath cooling, followed by a fifteen minute-stirring, addition of sodium azide (1.95 g) and 2-chlorophenylisocyanate (1.53 g) thereto and a sixteen hour-refluxing under heating in that order. After cooling, the reaction mixture was added with stirring to a mixture of sodium nitrite (2 g), water (200 ml) and ice (100 g) and the resulting mixture was acidified with 10% hydrochloric acid (until a potassium iodide starch paper became discolored), followed by extraction with ethyl acetate. The thus obtained ethyl acetate layer was washed with water, dried over sodium sulfate and evaporated under reduced pressure. The resulting residue was purified by flash column chromatography (eluent: hexane: ethyl acetate = 2:1) to obtain the desired 1-(2-chlorophenyl)-5(4H)-tetrazolinone (1.41 g) having a m.p. in the range of from 124.5° to 125.5° C. in a yield of 72% of theory.

Comparative Synthesis Example 2 (equi-molar ratio in Comparative Synthesis Example 1)

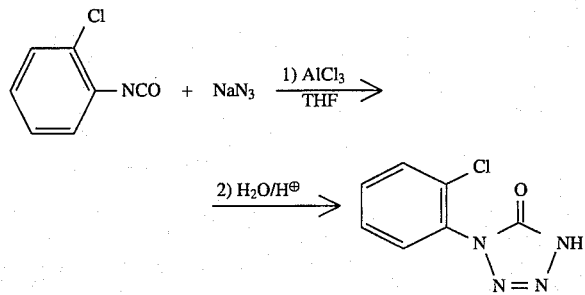

Anhydrous aluminum chloride (1.5 g) was added to tetrahydrofuran (30 ml) with ice bath cooling and the resulting mixture was stirred for fifteen minutes. To the mixture was added sodium azide (0.65 g) and 2-chlorophenylisocyanate (1.53 g), followed by a sixteen hour-refluxing. After cooling, the reaction mixture was added with stirring to a mixture of sodium nitrite (1 g), water (200 ml) and ice (100 g) and the resulting mixture was worked up in the same way as in Comparative Synthesis Example 1 to obtain the desired 1-(2-chlorophenyl)-5(4H)-tetrazolinone (0.5 g) having a m.p. in the range of from 124.5° to 125.5° C. in a yield of 25% of theory.

Comparative Synthesis Example 3 (J. Org. Chem., vol. 45, p. 5230, 1980)

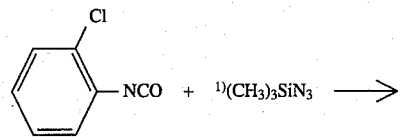 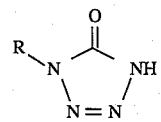

A mixture of 2-chlorophenylisocyanate (7 g) and trimethylsilyl azide (7.9 g) was refluxed under heating for either hours and then the mixture was evaporated to remove excess trimethylsilyl azide under reduced pressure distillation, followed by addition of methanol to the resulting residue. Thereafter, the methanol was distilled off under reduced pressure. The resulting residue was purified by flash column chromatography (eluent: hexane:ethyl acetate = 2:1) to obtain the desired 1-(2-chlorophenyl)-5(4H)-tetrazolinone (6.6 g) having a m.p. in the range of from 124° to 125.5° C., in a yield of 73% of theory.

These show that the process according to the present invention is economical regarding materials employed, efficiency of solvents, and yields of the desired products, so that it can be practically carried out on an industrial scale.

It will be appreciated that the instant specification and the claim are set forth by way of illustration and not limitation, and that various modifications and changes may be made without departing from the spirit and scope of the present invention.

We claim:

1. A process for the preparation of a 1-substituted-5(4H)-tetrazolinone of the formula $$\underset{N=N}{\overset{O}{\underset{\|}{R-N-C-NH}}} \quad (I)$$

wherein

R is $C_{1-6}$-alkyl, $C_{1-4}$ haloalkyl, $C_{1-8}$ cylcoalkyl, benzyl, phenethyl, phenyl, or phenyl substituted by $C_{1-4}$ alkyl, halogen, nitro, cyano, $C_{1-4}$ haloalkyl, $C_{1-4}$ alkoxy, $C_{1-4}$ alkoyxcarbonyl, $C_{1-4}$ alkylthio, phenoxy, $C_{1-4}$ haloalkoxy or $C_{1-4}$ haloalkylthio, which comprises reacting, in a polar solvent, an isocyanate of the formula $$RNCO \quad (II)$$

with sodium azide in an approximately equimolar ratio and in the presence of aluminum chloride, followed by addition of water and a mineral acid in excess.

2. The process according to claim 1, wherein the polar solvent comprises N,N-dimethyl formamide, N,N-dimethyl acetamide, N-methylpyrrolidone or 1,3-dimethylimidazolinone.

3. The process according to claim 1, wherein about 0.005 to 1.5 mols of aluminum are employed per mol of isocyanate of the formula (II).

4. The process according to claim 1, wherein about 0.01 to 1 mol of aluminum chloride is employed per mol of isocyanate of the formula (II).

* * * * *

UNITED STATES PATENT AND TRADEMARK OFFICE
CERTIFICATE OF CORRECTION

PATENT NO. : 5,530,135
DATED : June 25, 1996
INVENTOR(S) : Yanagi, et al.

It is certified that error appears in the above-indentified patent and that said Letters Patent is hereby corrected as shown below:

Col. 8, line 41   Delete " $C_{1-8}$ cylcoalkyl " and substitute -- $C_{3-8}$ cycloalkyl --

Signed and Sealed this

Thirty-first Day of December, 1996

Attest:

BRUCE LEHMAN

*Attesting Officer*            *Commissioner of Patents and Trademarks*